US012576183B2

(12) United States Patent
 Dhanaraj et al.

(10) Patent No.: US 12,576,183 B2
(45) Date of Patent: Mar. 17, 2026

(54) METHODS AND DEVICES FOR CHANGING THE FLOW RATES OF pH MODIFYING FLUIDS FOR CONTROLLING CROSS-LINKING RATES OF REACTIVE COMPONENTS OF BIOCOMPATIBLE SEALING COMPOSITIONS

(71) Applicant: ETHICON, INC., Raritan, NJ (US)

(72) Inventors: Sridevi Dhanaraj, Raritan, NJ (US);
 Salim Ghodbane, Raritan, NJ (US);
 Ashley Deanglis, Raritan, NJ (US);
 Michael Cardinale, Raritan, NJ (US);
 Nicole Smith, Raritan, NJ (US);
 Ashwin Viswanath, Raritan, NJ (US)

(73) Assignee: Ethicon, Inc., Raritan, NJ (US)

( * ) Notice: Subject to any disclaimer, the term of this patent is extended or adjusted under 35 U.S.C. 154(b) by 378 days.

(21) Appl. No.: 18/255,640

(22) PCT Filed: Dec. 3, 2021

(86) PCT No.: PCT/IB2021/061299
 § 371 (c)(1),
 (2) Date: Jun. 2, 2023

(87) PCT Pub. No.: WO2022/130103
 PCT Pub. Date: Jun. 23, 2022

(65) Prior Publication Data
 US 2024/0033399 A1 Feb. 1, 2024

Related U.S. Application Data

(60) Provisional application No. 63/127,308, filed on Dec. 18, 2020.

(51) Int. Cl.
 *A61L 24/04* (2006.01)
 *A61L 24/00* (2006.01)
 *A61L 24/10* (2006.01)

(52) U.S. Cl.
 CPC .......... *A61L 24/043* (2013.01); *A61L 24/001* (2013.01); *A61L 24/108* (2013.01)

(58) Field of Classification Search
 CPC .... A61L 24/001; A61L 24/043; A61L 24/108; A61L 2400/06; A61L 2400/14;
 (Continued)

(56) References Cited

U.S. PATENT DOCUMENTS 6,830,756 B2 12/2004 Hnojewyj
2001/0051813 A1* 12/2001 Hnojewyj .............. A61P 17/02
606/213
 (Continued)

FOREIGN PATENT DOCUMENTS

WO WO 2006/078282 A2 7/2006
WO WO 2008/016983 A2 2/2008

OTHER PUBLICATIONS

International Search Report relating to PCT International Patent Application No. PCT/IB2021/061299. Date of Mailing of International Search Report: Feb. 22, 2022.
 (Continued)

*Primary Examiner* — Robert A Lynch
(74) *Attorney, Agent, or Firm* — David R. Crichton; Leo B. Kriksunov

(57) ABSTRACT

A method of making a biocompatible composition for sealing tissue includes mixing a first fluid having a first reactive component (e.g., an electrophile) and a second fluid having a second reactive component (e.g., a nucleophile) to form a mixture and expressing the mixture. During expression, a pH modifying fluid (e.g., NaOH) is added to the mixture at a rate that changes. In one embodiment, a higher ratio of the pH modifying fluid is added to the mixture during a first expressing stage and a lower ratio of said pH modifying fluid is added to the mixture during a second expressing stage.
 (Continued)

During the first expressing stage, a mixing ratio of the pH modifying fluid, the first fluid and the second fluid is 0.7-1.4:1:1. During the second expressing stage, the mixing ratio of the pH modifying fluid, the first fluid and the second fluid is 0.12-0.24:1:1.

20 Claims, 9 Drawing Sheets

(58) Field of Classification Search
CPC ............. A61L 2400/18; A61L 2430/34; A61L 2430/40; A61M 5/16813; A61M 5/16827; A61M 5/16877; A61M 5/178; A61M 5/19; A61M 5/3129; A61M 5/3134; A61M 5/3135; A61M 2005/31598; A61M 11/00; A61M 11/007; A61B 17/00491; A61B 2017/00495; A61B 2017/00522; B05B 11/1083; B05B 11/1084; B05B 12/00; B05B 12/002; B05B 12/006; B05B 12/008; B05B 12/02; B05B 12/04; C08L 71/02; C08L 89/00
See application file for complete search history.

(56) References Cited

U.S. PATENT DOCUMENTS

| | | |
|---|---|---|
| 2002/0032463 A1 | 3/2002 | Cruise |
| 2015/0250463 A1* | 9/2015 | Jamiolkowski ..... B05B 11/1084 |
| | | 604/82 |

OTHER PUBLICATIONS

Written Opinion of PCT International Patent Application No. PCT/IB2021/061299. Date of Mailing of Written Opinion: Feb. 22, 2022.

* cited by examiner

METHODS AND DEVICES FOR CHANGING THE FLOW RATES OF pH MODIFYING FLUIDS FOR CONTROLLING CROSS-LINKING RATES OF REACTIVE COMPONENTS OF BIOCOMPATIBLE SEALING COMPOSITIONS

BACKGROUND OF THE INVENTION

Field of the Invention

The present patent application is generally related to biocompatible compositions used for sealing and hemostasis, and is more specifically related to systems, methods and devices for changing the flow rates of pH modifying fluids for controlling the cross-linking rates of reactive components of biocompatible sealing compositions.

Description of the Related Art

During a surgical procedure, incisions are created to access surgical sites. Once the surgical procedure has been completed, the incisions are closed for healing. In many instances, the incisions are closed with sutures or staples, however, tissue adhesives are also used for closing external incisions. In recent years, absorbable tissue adhesives have been developed for use in closing internal incisions.

Tissue adhesives and sealants include viscous gels that have little or no further curing after application, as well as compositions that solidify and/or cure once applied. Cyanoacrylates products such as Ethicon's Dermabond® and Covidien's Indermil® are examples of tissue adhesives that possess high strength and that cure in place. These materials polymerize to achieve the strength required, but do not offer the user any control of the degree of curing. Without providing the ability to control of the degree of curing, they typically address only one clinical need, e.g., to close and hold incisions.

Other products such as Ethicon's synthetic Omnex™ and biological Evicel® and Cryolife's BioGlue® are examples of sealants that act to prevent leakage. Once again, these materials typically address only one of the four clinical needs of acting as a sealant, acting as an adhesive, acting as a hemostatic agent, or acting as an adhesion preventing coating. The above-listed products do not offer the user the ability to change the performance characteristics to address different clinical needs.

Products such as Ethicon's Intercoat®, Genzyme's SepraGel®, Confluent's SprayGel®, and Covidien's Spray-Shield™, to name a few, are examples of adhesion barriers. These are either one of, or a combination of, hydrogels of PolyEthylene Glycol (PEG), Poly Vinyl Alcohol (PVA), CarboxyMethyl Cellulose (CMC), or Hyaluronic Acid (HLA). Once again, these materials typically only address one of the four clinical needs already discussed, in this case to act as an adhesions preventative. As before, these materials do not offer user the option to change the performance characteristics to address different clinical needs.

Although there may be some materials with properties mid-way between sealants and adhesion preventatives, their properties are not optimized for either application and they cannot be changed by the surgeon at the time of application during surgery. Many of the solutions that the art provides in the four areas of surgical adhesives, sealants, adhesion preventatives and hemostatic agents are based on cross-linkable systems. Initially, the product is flowable to allow application to a surgical site to be treated. After application, the product becomes non-flowable whereupon it stays in place to function properly.

The performance characteristics of the hydrogel products are intimately related to cross-link density. When cross-link density is high, mechanical strength is high and water swellability is low. High cross-link density hydrogels are often associated with products that function as adhesives. Sealants often require slightly less mechanical strength. As a result, hydrogels products in this category can have cross-link densities that are concomitantly slightly lower.

Finally a class of surgical adhesion preventatives based on hydrogel technology is cross-linked at a much lower level than the other two product classes. Their lower cross-link density allows a greater amount of swellability leading to a very slippery behavior. This latter characteristic has been identified by some to contribute to the ability to prevent viscera from adhering to one another or the initiation of collagen deposition leading to adhesion formations. Likewise, clinically relevant properties of some hemostatic agents depend on the mixing ratios of components. For example, the mixing ratios of fibrinogen and thrombin alter the properties of the resulting matrix.

The above-identified products provide pre-determined properties to address unique clinical needs, however, the products provide physicians with no flexibility or choice to alter or dial in the properties for other clinical needs at the time of application during surgery.

There have been some attempts to overcome the above-noted deficiencies. For example, US 2015/0250463, assigned to Ethicon, Inc. of Somerville, New Jersey, the disclosure of which is hereby incorporated by reference herein, teaches a method of applying a coating onto tissue. The coating has at least two physiologically distinct layers that are delivered from a single device by delivery of a multi-part biomedical composition in different blended or mixing ratios. Disclosed methods include connecting at least two syringe barrels that contain inter-reacting components of the multi-part biomedical composition. Each syringe barrel has a piston that is internally slidable for expression of the components. The first syringe has a first retention compartment and a second retention compartment that are spaced axially therein, with a gasket positioned in the first retention compartment. The method includes advancing the pistons through each syringe to express onto a surface the reactive components of the multi-part biomedical composition in a first blended or mixing ratio, and continuing to advance the pistons to disengage a gasket from the piston of a first syringe at a point between the first retention compartment and the second retention compartment, and still further advancing the pistons through each syringe to express the reactive components of the multi-part biomedical composition in a second blended or mixing ratio to form a biomedical coating having physiologically distinct layers.

U.S. Pat. No. 6,830,756 to Hnojewyj discloses systems, methods, and compositions for achieving closure of vascular puncture sites. The systems and methods form a vascular closure composition by mixing together a first component, a second component, and a buffer material. The first component includes an electrophilic polymer material having a functionality of at least three. The second component includes a nucleophilic material that, when mixed with the first component within a reaction pH range of between 7 to 9, cross-links with the first component to form a non-liquid, three-dimensional barrier. The buffer material has a pH within the reaction pH range. The systems and methods apply the composition to seal a vascular puncture site.

In spite of the above-identified advances, there remains a need for improved systems, devices and methods for controlling the cross-linking rates of the reactive components of sealing compositions for effectively sealing tissue and hemostasis.

SUMMARY OF THE INVENTION

The present patent application is directed to biocompatible sealing compositions, which may include sealing agents, adhesives, and hemostatic agents. In one embodiment, systems, devices and methods are used for delivering sealants, whereby the structure and properties of the sealing composition may change across the thickness of the composition.

In one embodiment, the present patent application is also directed to delivering biocompatible sealing compositions including sealing agents, adhesives, and hemostatic agents from a single applicator instrument. In one embodiment, medical professionals may select the properties and function desired for the sealant at the time of delivery of the sealant to a surface of tissue.

The systems, devices and methods disclosed herein provide surgeons and/or users with applicator instruments for dispensing biocompatible sealing compositions, whereby the mixing ratio of the components forming the sealant changes during expression resulting in the formation of a sealant composition having physiologically distinct layers or zones.

In one embodiment, a method of making a biocompatible composition for sealing tissue preferably includes mixing a first fluid having a first reactive component and a second fluid having a second reactive component to form a mixture, and expressing the mixture of the first and second fluids. In one embodiment, during the expressing the mixture step, a pH modifying fluid is desirably added to the mixture. In one embodiment, the rate at which the pH modifying fluid is added to the mixture changes during the expressing step for changing cross-linking reaction rates between the first and second reactive components.

In one embodiment, a higher ratio of the pH modifying fluid is added to the mixture during a first stage of the expressing the mixture step and a lower ratio of the pH modifying fluid is added to the mixture during a second stage of the expressing the mixture step.

In one embodiment, each of the first and second fluids is expressed at a uniform flow rate throughout the expressing the mixture step, and the pH modifying fluid has a higher flow rate during the first stage of the expressing the mixture step and a lower flow rate during the second stage of the expressing the mixture step.

In one embodiment, the higher flow rate of the pH modifying fluid may be 3-6 mL/minute and the lower flow rate of the pH modifying fluid may be 0.5-1.0 mL/minute.

In one embodiment, during the first stage of the expressing the mixture step, a mixing ratio of the pH modifying fluid, the first fluid and the second fluid is 0.7-1.4:1:1.

In one embodiment, during the second stage of the expressing the mixture step, the mixing ratio of the pH modifying fluid, the first fluid and the second fluid is 0.12-0.24:1:1.

In one embodiment, during the first stage of the expressing the mixture step, the first and second reactive components have a higher cross-linking rate, and during the second stage of the expressing the mixture step, the first and second reactive components have a lower cross-linking rate.

In one embodiment, the expressing the mixture step may include spraying or dripping the mixture onto a surface to form the biocompatible sealing composition on the surface.

In one embodiment, the first reactive component desirably includes an electrophilic polymer material.

In one embodiment, the electrophilic polymer material may be electrophilic PEG and the nucleophilic material may be PEG-Amine or albumin.

In one embodiment, the electrophilic PEG may be PEG-NHS.

In one embodiment, the second reactive component preferably includes a nucleophilic material.

In one embodiment, the pH modifying fluid has a pH level of between pH 10-pH 14.

In one embodiment, the pH modifying fluid may include NaOH.

In one embodiment, the first fluid desirably includes 150 mg/mL 4 Arm PEG-SG-20K and 100 mM carbonate buffer having pH 9.0, the second fluid desirably includes 200 mg/ml albumin in water, and the pH modifying fluid preferably includes 1N NaOH.

In one embodiment, each of the first and second fluids is preferably expressed at a uniform flow rate throughout the expressing the mixture step. In one embodiment, the pH modifying fluid may have a lower flow rate during the first stage of the expressing the mixture step and a higher flow rate during the second stage of the expressing the mixture step.

In one embodiment, during the first stage of the expressing the mixture step, the first and second reactive components have a lower cross-linking rate, and during the second stage of the expressing the mixture step, the first and second reactive components have a higher cross-linking rate.

In one embodiment, the lower flow rate of the pH modifying fluid is preferably 0.5-1.0 mL/minute and the higher flow rate of the pH modifying fluid is preferably 3-6 mL/minute.

In one embodiment, during the first stage of the expressing the mixture step, a mixing ratio of the pH modifying fluid, the first fluid and the second fluid is preferably about 0.12-0.24:1:1.

In one embodiment, during the second stage of the expressing the mixture step, the mixing ratio of the pH modifying fluid, the first fluid and the second fluid is preferably about 0.7-1.4:1:1.

In one embodiment, a method of making a biocompatible sealing composition preferably includes mixing a first fluid having a first reactive component, a second fluid having a second reactive component, and a pH modifying fluid to form a mixture, and expressing the mixture of the first fluid, the second fluid, and the pH modifying fluid to form the biocompatible sealing composition having different zones with different rates of cross-linking. In one embodiment, during the expressing the mixture step, the mixing ratio of the pH modifying fluid relative to the first and second fluids is changed for modifying cross-linking rates of the first and second fluids throughout the different zones of the biocompatible sealing composition.

In one embodiment, during one stage of the expressing the mixture step, a mixing ratio of the pH modifying fluid, the first fluid and the second fluid is about 0.7-1.4:1:1, and during another stage of the expressing the mixture step, the mixing ratio of the pH modifying fluid, the first fluid and the second fluid is about 0.12-0.24:1:1.

In one embodiment, the first reactive component comprises an electrophile, the second reactive component comprises a nucleophile, and the pH modifying fluid comprises NaOH having a pH level of between 10-14 pH.

In one embodiment, an applicator instrument for expressing a multi-part biocompatible sealing composition preferably includes a first chamber containing a first fluid having a first reactive component, a second chamber containing a second fluid having a second reactive component, and a third chamber containing a pH modifying fluid.

In one embodiment, the applicator instrument preferably includes a mixing chamber for mixing the first fluid, the second fluid and the pH modifying fluid into a mixture, and a nozzle in fluid communication with the mixing chamber for expressing the mixture.

In one embodiment, the applicator instrument desirably includes a flow rate adjusting system connected with the third chamber for changing the flow rate at which the pH modifying fluid is added to the first and second fluids within the mixing chamber.

In one embodiment, a cross-sectional diameter of the third chamber changes along a length of the third chamber.

These and other preferred embodiments of the present patent application will be described in more detail herein.

DETAILED DESCRIPTION OF PREFERRED EMBODIMENTS

Figure 1:
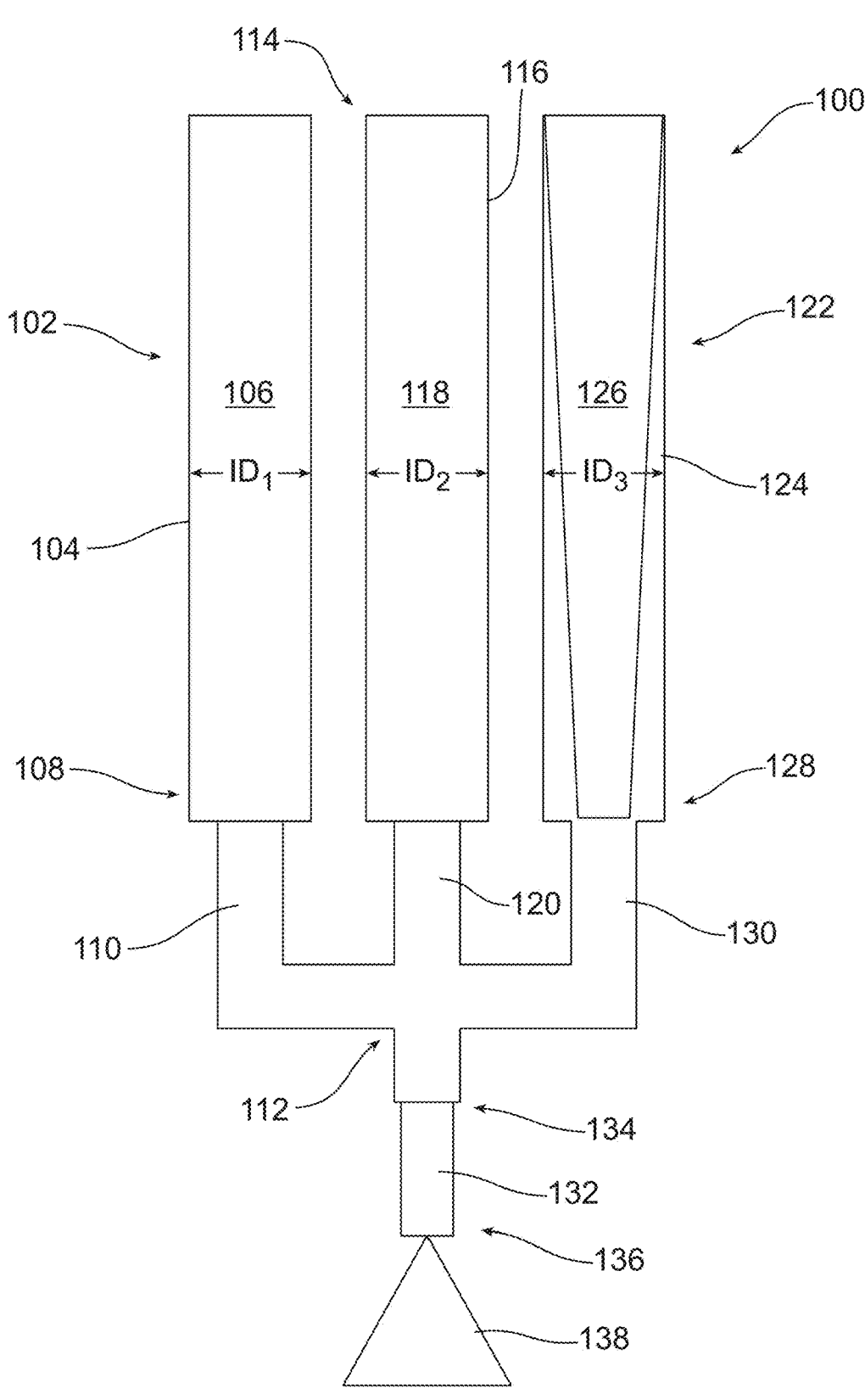
FIG. 1 is a schematic view of an applicator instrument used for mixing a first fluid having a first reactive component, a second fluid having a second reactive component, and a pH modifying fluid, whereby the rate at which the pH modifying fluid is added to the mixture is reduced between a first stage and a second stage, in accordance with one embodiment of the present patent application.

Referring to FIG. 1, in one embodiment, an applicator instrument 100 for dispensing a biocompatible sealing composition that is used for sealing tissue and/or hemostasis preferably includes a first syringe 102 having a first barrel 104 that defines a first chamber 106. In one embodiment, the first chamber 106 is adapted to receive a first fluid having a first reactive component (e.g., an electrophile). The first barrel 104 preferably has a distal end 108 that is in fluid communication with a first dispensing conduit 110, which is configured to direct the first fluid into a mixing chamber 112 of the applicator instrument 100. In one embodiment, the inner diameter $ID_1$ of the first barrel 104 preferably remains constant between the proximal end and the distal end 108 thereof. Although not shown, a rod and piston may be used for forcing the first fluid from the distal end 108 of the first barrel 104.

In one embodiment, the applicator instrument 100 preferably includes a second syringe 114 having a second barrel 116 that defines a second chamber 118. In one embodiment, the second chamber 118 is adapted to receive a second fluid having a second reactive component (e.g., a nucleophile). The second barrel 116 preferably has a distal end that is in fluid communication with a second dispensing conduit 120, which is configured to direct the second fluid into the mixing chamber 112 of the applicator instrument 100, whereby the first and second fluids are mixed together and react to form the biocompatible sealing composition. In one embodiment, the inner diameter $ID_2$ of the second barrel 116 desirably remains constant between the proximal end and the distal end thereof. Although not shown, a rod and piston may be used for forcing the second fluid from the distal end of the second barrel 114.

In one embodiment, the first and second syringes 102, 114 may have a standard syringe construction with a hollow cylindrical barrel of the same diameter throughout, which will provide a constant relative expression rate.

In one embodiment, the inner diameters $ID_1$ and $ID_2$ of the respective first and second barrels 104, 116 are the same. In one embodiment, the first and second fluids may be jointly expressed in a constant ratio (e.g., a constant flow rate). In one embodiment, the first and second fluids may be jointly expressed in a 1:1 ratio.

In one embodiment, the applicator instrument 100 preferably includes a third syringe 122 having a third barrel 124 that defines a third chamber 126. In one embodiment, the third chamber 126 is adapted to receive a pH modifying fluid (e.g., NaOH having a 10-14 pH), which is added into the mixture of the first and second fluids for controlling the rate of cross-linking of the first and second reactive components of the respective first and second fluids. The third barrel 124 preferably has a distal end 128 that is in fluid communication with a third dispensing conduit 130, which is configured to direct the pH modifying fluid into the mixing chamber 112 of the applicator instrument 100. In one embodiment, the inner diameter $ID_3$ of the third barrel 124 desirably changes in size between the proximal end and the distal end 128 thereof, which changes and/or varies the flow rate of the pH modifying fluid that is added into the mixing chamber 112 of the applicator instrument 100. In one embodiment, the inner diameter $ID_3$ of the third barrel 124 is larger at the proximal end thereof and smaller at the distal end 128 thereof. In one embodiment, the inner diameter $ID_3$ of the third barrel 124 gradually reduces in size between the proximal end and the distal end 128 thereof.

In one embodiment, the applicator instrument 100 preferably includes a nozzle 132 having a proximal end 134 that is in fluid communication with the mixing chamber 112 and a distal end 136 that has one or more dispensing orifices that are adapted to dispense a mixture of the first fluid, the second fluid, and the pH modifying fluid. In one embodiment, the mixture of the first fluid, the second fluid, and the pH modifying fluid may be dispensed as a spray that is directed toward a target on a surface (e.g., a tissue surface; a blood vessel). In one embodiment, the nozzle 132 may be adapted to drip the mixture of the first fluid, the second fluid, and the pH modifying fluid onto a surface. The expressed mixture preferably forms a sealing mass 138 that is applied onto a target such as tissue of a patient.

In one embodiment, the nozzle 132 is connected to the mixing chamber 112 for intermixing and simultaneous expression of the resulting mixture through one or more dispensing orifices. In one embodiment, no mixing chamber is used and the components are simultaneously expressed through the nozzle without mixing, whereupon the components react with one another to form a tissue sealant.

In one embodiment, prior to being expressed from the nozzle 132 of the applicator instrument 100, the first fluid having the first reactive component and the second fluid having the second reactive component are mixed together in the mixing chamber 112. The pH modifying fluid in the third chamber 126 is added to the mixture of the first and second fluids in a changing ratio. In one embodiment, a higher rate of pH modifying fluid is added to the mixture at the beginning of an expression and a lower rate of the pH modifying fluid is added to the mixture at the end of the expression. At the higher rate of adding the pH modifying fluid, the cross-linking of the first and second reactive components occurs at a higher and/or faster rate. At the lower rate of adding the pH modifying fluid, the cross-linking of the first and second reactive components occurs at a lower and/or slower rate.

In one embodiment, the first fluid having the first reactive component preferably includes an electrophile. In one embodiment, the electrophile may include electrophilic materials such as electrophilic polyethylene glycols including polyethylene glycols functionalized with activated NHS esters, which may include, but are not limited to, succinimidyl glutarate (PEG-SG), succinimidyl succinate, succinimidyl sebecate, and succinimidyl carbonate. In one embodiment, the electrophilic PEG may be comprised of 2, 3, 4, 6, 8 arms, etc., having a molecular weight from about 1000 to 20,000 Daltons.

In one embodiment, the first fluid with the first reactive component preferably includes a buffer. The buffer may include any alkaline buffer such as phosphate, carbonate, bicarbonate, or a borate buffer. In one embodiment, the buffer is a 100 mM carbonate buffer having 9.0 pH.

In one embodiment, the second fluid having the second reactive component preferably includes a nucleophile. In one embodiment, the nucleophile may include an electrophilic material such as an electrophilic PEG. In one embodiment, the electrophilic PEG may be comprised of 2, 3, 4, 6, 8 arms, etc., having a molecular weight from about 1000 to 20,000 Daltons. In one embodiment, the nucleophile may be formed of either biological or synthetic materials. Synthetic materials may include, but are not limited to, nucleophilic polyethylene glycols functionalized with Amine or Thiol reactive groups. Biologically derived nucleophiles may include, but are not limited to, proteinaceous components, such as albumin. The albumin component may be natural, such as human serum albumin, or recombinantly produced albumin.

In one embodiment, the pH modifying fluid may be any strong base including, but not limited to, potassium hydroxide, sodium hydroxide, or calcium hydroxide. In one embodiment, the pH modifying fluid has a pH level of between 10-14 pH. In one embodiment, the pH modifying fluid is NaOH (e.g., 1N NaOH), which is preferably delivered at varying rates.

In one embodiment, a higher ratio of the pH modifying fluid is added to the mixture during a first stage of an expressing the mixture step and a lower ratio of the pH modifying fluid is added to the mixture during a second stage of the expressing the mixture step.

In one embodiment, each of the first and second fluids is expressed at a uniform flow rate throughout an expressing the mixture step, and the pH modifying fluid has a higher flow rate during a first stage (e.g., the beginning) of the expressing the mixture step and a lower flow rate during a second stage (e.g., the ending) of the expressing the mixture step.

In one embodiment, the higher flow rate of the pH modifying fluid is 3-6 mL/minute and the lower flow rate of said pH modifying fluid is 0.5-1.0 mL/minute.

In one embodiment, during the first stage of the expressing the mixture step, a mixing ratio of the pH modifying fluid, the first fluid and the second fluid is 0.7-1.4:1:1. In one embodiment, during the second stage of the expressing the mixture step, the mixing ratio of the pH modifying fluid, the first fluid and the second fluid is 0.12-0.24:1:1. Thus, in one embodiment, the pH modifying fluid is added at a higher rate during the first stage and at a lower rate during the second stage of the expressing the mixture step.

In one embodiment, during the first stage of the expressing the mixture step, the first and second reactive components have a higher cross-linking rate. In one embodiment, during the second stage of the expressing the mixture step, the first and second reactive components have a lower cross-linking rate. The different cross-linking rates will affect the structure of the biocompatible sealing composition that is formed on a surface (e.g., a tissue surface).

Experiment. A study was conducted to assess the advantages of concentration gradient of a sealant formulation with a cross-linking rate modifier. Applicator instruments, similar to those shown and described above in FIG. 1, were utilized to complete the study. An electrophilic fluid comprising 150 mg/mL 4 Arm PEG-SG-20k, 100 mM carbonate buffer (pH=9.0) and a nucleophilic fluid comprising 200 mg/mL albumin in water and were loaded into separate barrels of an applicator instrument (e.g., an applicator device sold under the trademark EVICEL®, owned by Ethicon, Inc. of Somerville, New Jersey). The applicator instrument was connected to a dispensing nozzle and loaded into a syringe pump that was set to deliver a uniform flow rate of 5.8 mL/min (i.e., 4.25 mL/min of each component). A pH modifying fluid, 1N NaOH, was loaded into a 60 ml syringe and coupled with a different syringe pump. The syringe was connected to tubing that was connected to the gas inlet of the dispensing nozzle of the applicator instrument.

Figure 2:
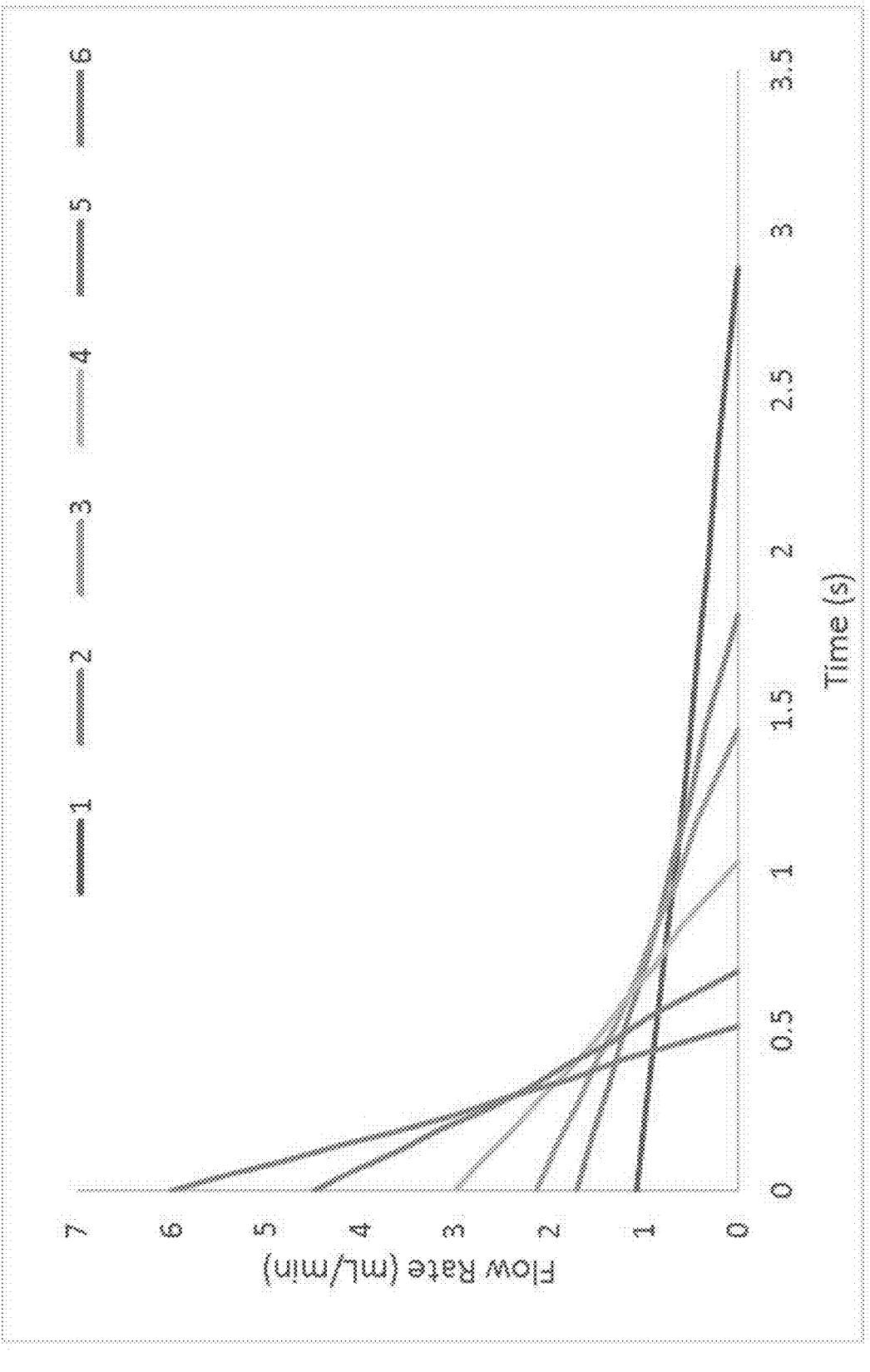
FIG. 2 is a chart showing different flow rates or gradients at which pH modifying fluids are added to mixtures of first fluids having a first reactive components and second fluids having second reactive components for controlling the rates of cross-linking of the first and second reactive components, in accordance with one embodiment of the present patent application.

The rate of the NaOH (i.e., the pH modifying fluid) expression was programmed to six different Gradients, as shown in the graph in FIG. 2. The Gradients included different rates of change for adding the pH modifying fluid, however, the total volume of NaOH for each Gradient was held constant at about 30 μL. The six different Gradients had a higher initial flow rate and a lower ending flow rate. Gradient #1 had an initial flow rate of 1 mL/minute. Gradient #2 had an initial flow rate of 1.8 mL/minute. Gradient #3 had an initial flow rate of 2.2 mL/minute. Gradient #4 had an initial flow rate of 3 mL/minute. Gradient #5 had an initial flow rate of 4.6 mL/minute. Gradient #6 had an initial flow rate of 6 mL/minute.

pH Measurement. The different flow rate profiles were generated as described above without PEG-SG-20k. During one expression, five aliquots were taken. The pH of the solution was tested with a Horiba Laquatwin Compact pH (Model Laquatwin-pH-33).

Figure 3:
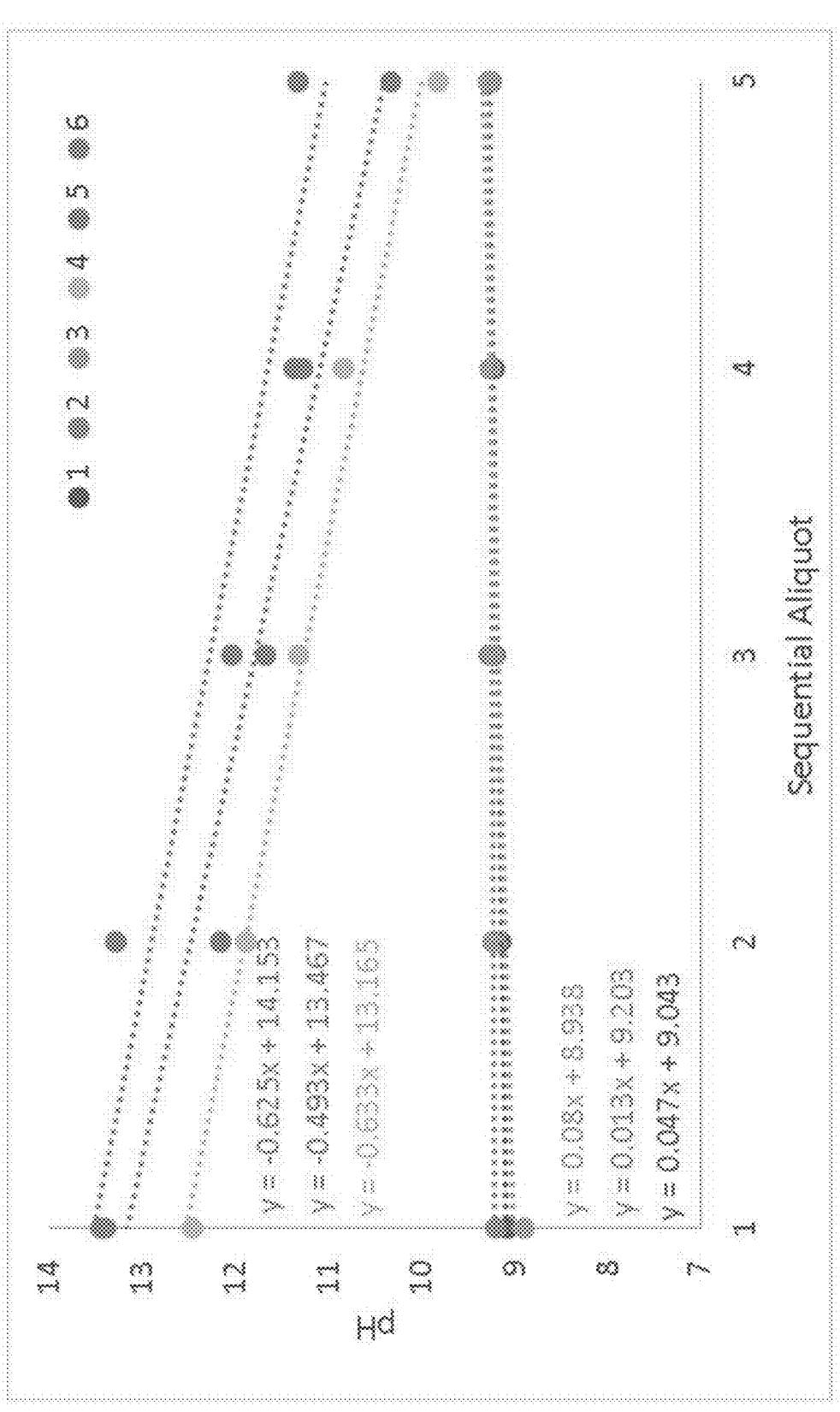
FIG. 3 is a chart showing the pH changes at the different flow rates or gradients depicted in FIG. 2, in accordance with one embodiment of the present patent application.

Referring to the graph shown in FIG. 3, the different rates of NaOH expression for Gradient #s 1-6 resulted in pH shifts of the formulation. A regression analysis of each of the pH profiles found that Gradient #s 2 and 3 did not have a non-zero slope (p>0.1). Gradient #1 did have a significant non-zero slope (p<0.01), however, the pH gradient was practically insignificant as the rate of pH change was 0.05 units per aliquot.

On the other hand, Gradient #s 4, 5, and 6 demonstrated non-zero slopes (p=0.00, 0.00, and 0.01). However, there was no statistical difference between the slopes, as determined by overlapping confidence intervals (Table 1). The pH profiles between Gradient #s 4-6 were offset from each other.

Polymer Travel Distance. Polymer travel distance provides a characterization of the flowability of a sealant. The different flow rate profiles were generated as described above. The dispensing nozzle of the applicator instrument was held at one location for the entire sealant expression on a 20° incline glass plate. This was repeated six times per formulation (i.e., six times for each of Gradient #s 1-6). The linear distance that each formulation traveled down the plane was measured using a ruler and recorded. In one embodiment, less travel distance is desirable and equates with a more effective tissue sealant.

Figure 4:
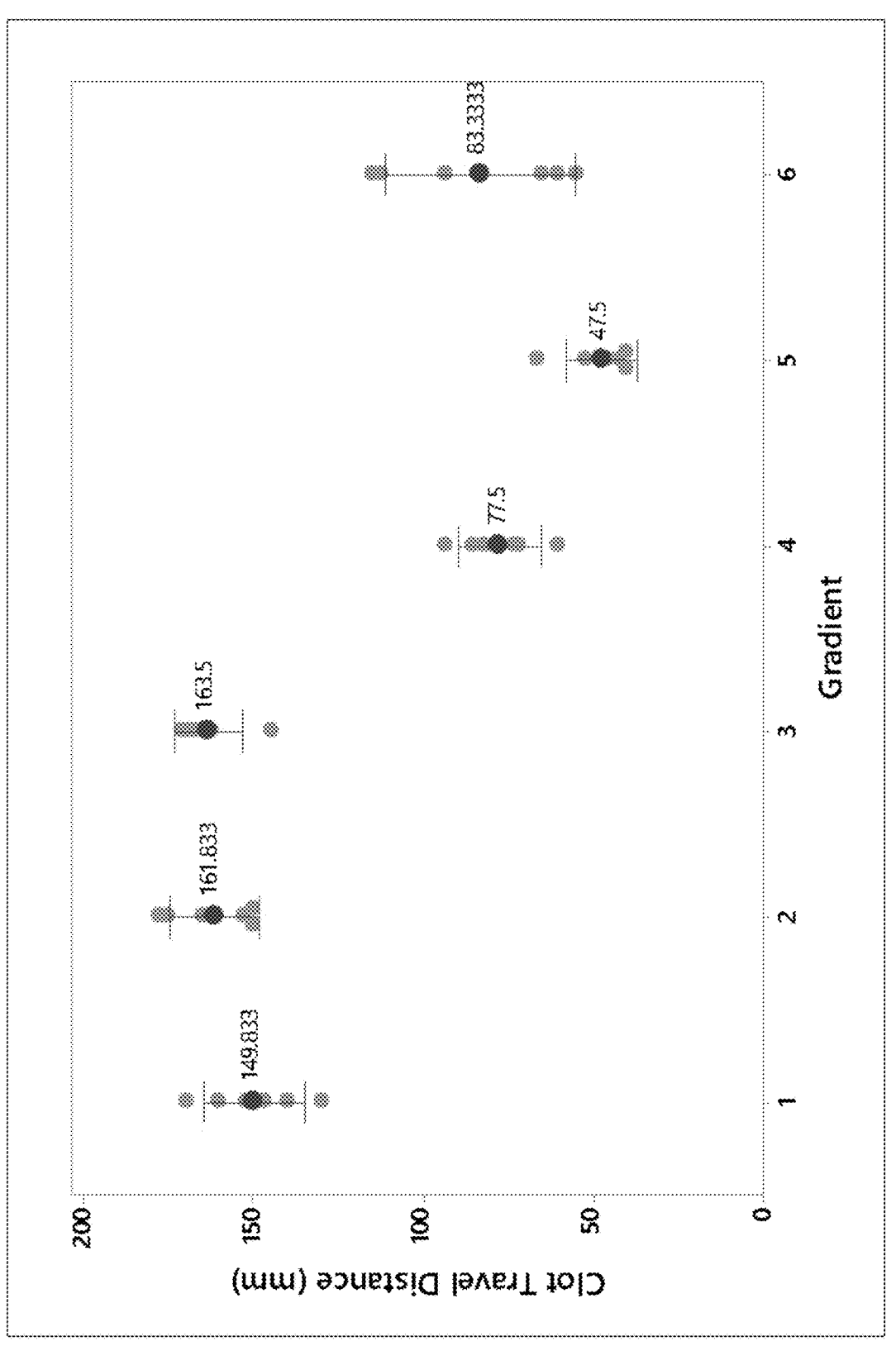
FIG. 4 is a chart showing travel distances of respective sealing compositions that are formed using the different flow rates or gradients of the pH modifying fluids shown in FIG. 2, in accordance with one embodiment of the present patent application.

Referring to the graph in FIG. 4, polymer travel distance testing demonstrated that modifying the rate at which the pH modifying fluid was added to the mixture of the electrophilic and nucleophilic components had a significant effect on polymerization time (one-way ANOVA, p<0.01). A significantly reduced polymer travel distance was observed with Gradient #s 4, 5, and 6 compared to Gradient #s 1, 2, and 3 (post-hoc Tukey's test). In addition, Gradient #5 demonstrated a significantly reduced polymer travel distance (post-hoc Tukey's test) relative to all other gradients tested with a 69% reduction in travel distance relative to Gradient #s 1, 2 and 3 and an approximately 40% reduction in travel distance relative to Gradient #s 4 and 6.

The study showed that there is a significant effect on pH profile and polymer travel distance by the gradient application of a pH modifier. When holding the volume of the pH modifier constant, the slope of the gradient can significantly modulate these properties. When the gradient is too gradual, as shown for Gradient #s 1, 2, and 3 (FIG. 2), the effect of the gradient is not significant. However, when the gradient changed rapidly (i.e., Gradient #s 4, 5, and 6), a pH gradient was formed. Within the rapid gradients tested (i.e., Gradient #s 4, 5, and 6), it was found that there was a more preferable gradient (i.e., Gradient #5), which resulted in a 40% more localized sealant, as demonstrated by the polymer travel distances shown in FIG. 4.

The study indicates that there is a higher rate of cross-linking and polymerization when there is an increase in the slope of the gradient. At a certain point, however, the pH of the system is too high, which leads to hydrolysis of the reactive groups before polymerization can occur.

Figure 5:
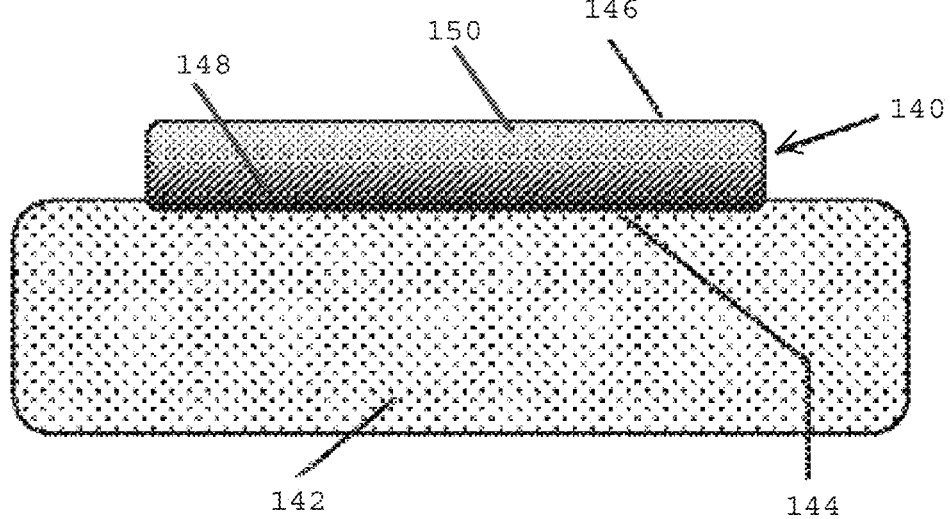
FIG. 5 shows a biocompatible sealing composition resulting from a decrease in the rate at which a pH modifying fluid is added to a mixture of a first fluid having a first reactive component and a second fluid having a second reactive component, in accordance with one embodiment of the present patent application.

FIG. 5 shows a biocompatible sealing composition 140 that has been formed on tissue 142, which has been created using the applicator instrument 100 (FIG. 1) and the flow rate ratios described above for Gradient #5 (FIGS. 2-5). The biocompatible sealing composition 140 has a bottom surface 144 that faces toward the tissue 142 and a top surface 146 that faces away from the tissue 142. The biocompatible sealing composition 140 formed on the tissue 142 has a mixing ratio of components gradually changing from a higher cross-linking percentage within a bottom zone 148 of the sealing composition 140 to a lower cross-linking percentage within a top zone 150 of the sealing composition 140. The gradual change in cross-linking is schematically indicated in FIG. 5 by a shading gradient from darker for representing a higher rate of cross-linkage to lighter for representing a lower rate of cross-linkage.

Figure 6:
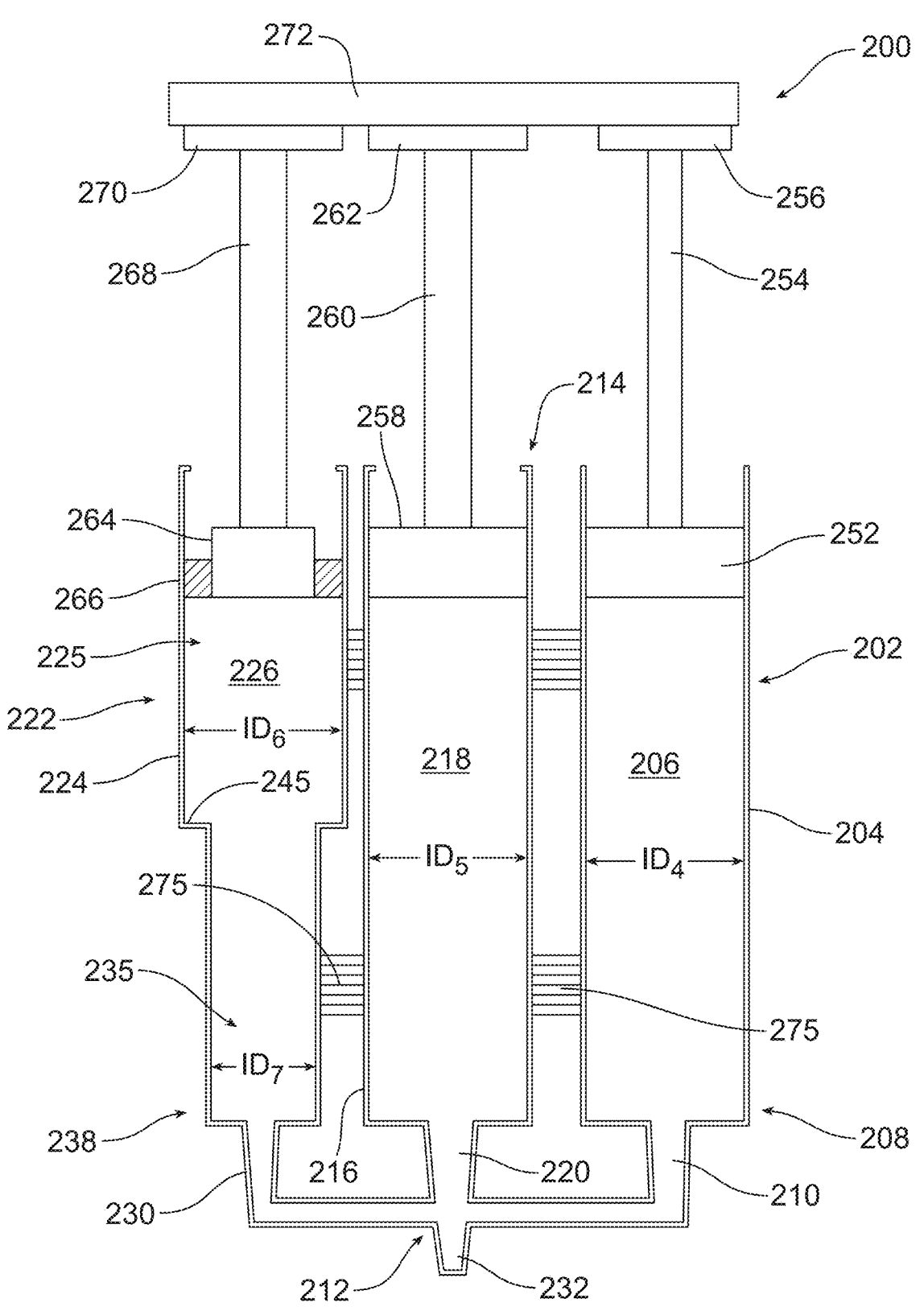
FIG. 6 is a schematic view of an applicator instrument used for mixing a first fluid having a first reactive component, a second fluid having a second reactive component, and a pH modifying fluid, whereby the rate at which the pH modifying fluid is added to the mixture is reduced in steps between a first stage and a second stage, in accordance with one embodiment of the present patent application.

Referring to FIG. 6, in one embodiment, an applicator instrument 200 may be configured to change the rate at which a pH modifying fluid is added to a reactive mixture in steps, rather than changing the rate gradually. In one embodiment, the applicator instrument 200 preferably includes a first syringe 202 having a first barrel 204 that defines a first chamber 206. The first chamber 206 is adapted to receive a first fluid having a first reactive component (e.g., an electrophile). The first barrel 204 preferably has a distal end 208 that is in fluid communication with a first dispensing conduit 210, which is configured to direct the first fluid into a mixing chamber 212 of the applicator instrument 200. In one embodiment, the inner diameter $ID_4$ of the first barrel 204 preferably remains constant between the proximal end and the distal end 208 thereof. A first piston 252, a first rod 254, and a first handle 256 may be used for forcing the first fluid from the distal end 208 of the first barrel 204 and into the mixing chamber 212.

In one embodiment, the applicator instrument 200 preferably includes a second syringe 214 having a second barrel 216 that defines a second chamber 218. In one embodiment, the second barrel 218 is adapted to receive a second fluid having a second reactive component (e.g., a nucleophile). The second barrel 216 preferably has a distal end that is in fluid communication with a second dispensing conduit 220, which is configured to direct the second fluid into the mixing chamber 212 of the applicator instrument 200, whereby the first and second fluids are mixed together and react to form the biocompatible sealing composition. In one embodiment, the inner diameter $ID_5$ of the second barrel 216 desirably remains constant between the proximal end and the distal end thereof. A second piston 258, a second rod 260, and a second handle 262 may be used for forcing the second fluid from the distal end of the second barrel 204 and into the mixing chamber 212.

In one embodiment, the inner diameters $ID_4$ and $ID_5$ of the respective first and second barrels 204, 216 are the same. In one embodiment, the first and second fluids may be jointly expressed in a constant ratio (e.g., a constant flow rate). In one embodiment, the first and second fluids may be jointly expressed in a 1:1 ratio.

In one embodiment, the applicator instrument 200 preferably includes a third syringe 222 having a third barrel 224 that defines a third chamber 226. In one embodiment, the third chamber 226 is adapted to receive a pH modifying fluid (e.g., NaOH having a 10-14 pH), which is added into the mixture of the first and second fluids for controlling the rate of cross-linking of the first and second reactive components of the respective first and second fluids. The third barrel 224 preferably has a distal end 228 that is in fluid communication with a third dispensing conduit 230, which is configured to direct the pH modifying fluid into the mixing chamber 212 of the applicator instrument 200. In one embodiment, the inner diameter of the third barrel 224 desirably changes in size (i.e., in steps) between the proximal end and the distal end 228 thereof, which results in step change adjustments for the flow rate of the pH modifying fluid that is added into the mixing chamber 212 of the applicator instrument 200. In one embodiment, the third barrel 224 has a larger diameter section 225 having an inner diameter $ID_6$, a smaller diameter section 235 having an inner diameter $ID_7$, and a stop surface 245 that extends between the distal end of the larger diameter section 225 and the proximal end of the smaller diameter section 235. A third piston 264, a gasket 266 surrounding the third piston 264, a third rod 268, and a third handle 270 may be used for forcing the third fluid from the distal end 228 of the third barrel 224 and into the mixing chamber 212.

In one embodiment, the barrels 204, 216 and 224 of the respective syringes 202, 214, and 222 may be joined side-by-side by connecting structure 275 that interconnects adjacent barrels.

In one embodiment, the applicator instrument 200 preferably includes a nozzle 232 that is in fluid communication with the mixing chamber 212. In one embodiment, the nozzle 232 preferably has one or more dispensing orifices that are adapted to dispense a mixture of the first fluid, the second fluid, and the pH modifying fluid. In one embodiment, the mixture of the first fluid, the second fluid, and the pH modifying fluid may be dispensed as a spray that is directed toward a target on a surface (e.g., a tissue surface; a blood vessel). In one embodiment, the nozzle 232 may be adapted to drip the mixture of the first fluid, the second fluid, and the pH modifying fluid onto a surface. The expressed mixture preferably forms a biocompatible sealing formulation that is applied onto a target such as tissue of a patient.

In one embodiment, the applicator instrument 200 preferably includes a bar 272 that may be interconnected with the first, second and third handles 256, 262, 270 to ensure joint movement of the respective first, second, and third pistons 252, 258, 264 to provide for simultaneous expression of the first fluid having the first reactive component, the second fluid having the second reactive component, and the pH modifying fluid.

In the embodiment shown in FIG. 6, the initial relative expression ratio of the first fluid having the first reactive component, the second fluid having the second reactive component, and the pH modifying fluid may be about 1:1:0.7-1.4 and corresponds to the position of the third piston 264 and the gasket 266 in the larger diameter compartment 225 of the third syringe 222. As expression of the first fluid, second fluid, and pH modifier progresses, the third piston 264 reaches the smaller diameter compartment 235 of the third barrel 224 of third syringe 222 and disengages from the gasket 266, whereby the relative expression rate of the pH modifying fluid decreases, while the relative expression rate of the first fluid and the second fluid remains unchanged.

In one embodiment, prior to being expressed from the nozzle 132 of the applicator instrument 100, the first fluid having the first reactive component and the second fluid having the second reactive component are mixed together in the mixing chamber 112. The pH modifying fluid in the third chamber 126 is added to the mixture of the first and second fluids in a changing ratio. In one embodiment, a higher rate of pH modifying fluid is added to the mixture at the beginning of an expression and a lower rate of the pH modifying fluid is added to the mixture at the end of the expression. At the higher rate of adding the pH modifying fluid, the cross-linking of the first and second reactive components occurs at a higher and/or faster rate. At the lower rate of adding the pH modifying fluid, the cross-linking of the first and second reactive components occurs at a lower and/or slower rate.

Figure 7:
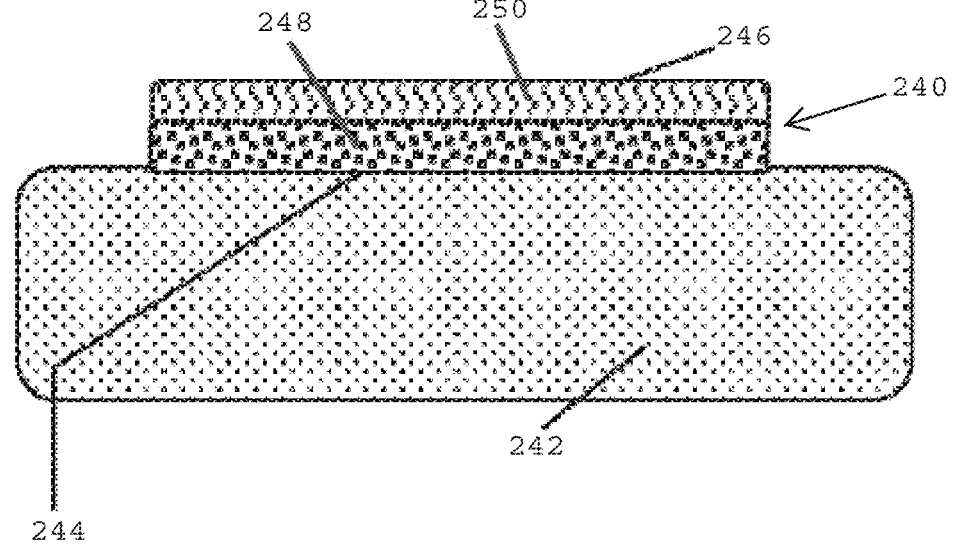
FIG. 7 shows a biocompatible sealing composition that is formed using the applicator instrument of FIG. 6 and resulting from a step change in the rate at which a pH modifying fluid is added to a mixture of a first fluid having a first reactive component and a second fluid having a second reactive component, in accordance with one embodiment of the present patent application.

FIG. 7 shows a biocompatible sealing composition 240 that has been formed on tissue 242, which has been created using the applicator instrument 200 and the step flow rate adjustments of the pH modifying fluid as described above for the applicator instrument shown in FIG. 6. The biocompatible sealing composition 140 has a mixing ratio of components changing step-wise from a higher cross-linking percentage to a lower cross-linking percentage, resulting in a first zone 248, adjacent tissue surface 244, having a higher cross-linking concentration, and a step-wise change to a second zone 250, adjacent a top surface 246 of the sealing composition, having a lower cross-linking concentration. In one embodiment, the first and second zones 248, 250 are physically distinct layers in which the composition of the zones is different. Moreover, the first and second zones 248, 250 are physiologically distinct in a sense that their interaction with tissue is different due to the different properties of the zones resulting from mixing the components in different mixing ratios.

Figure 8:
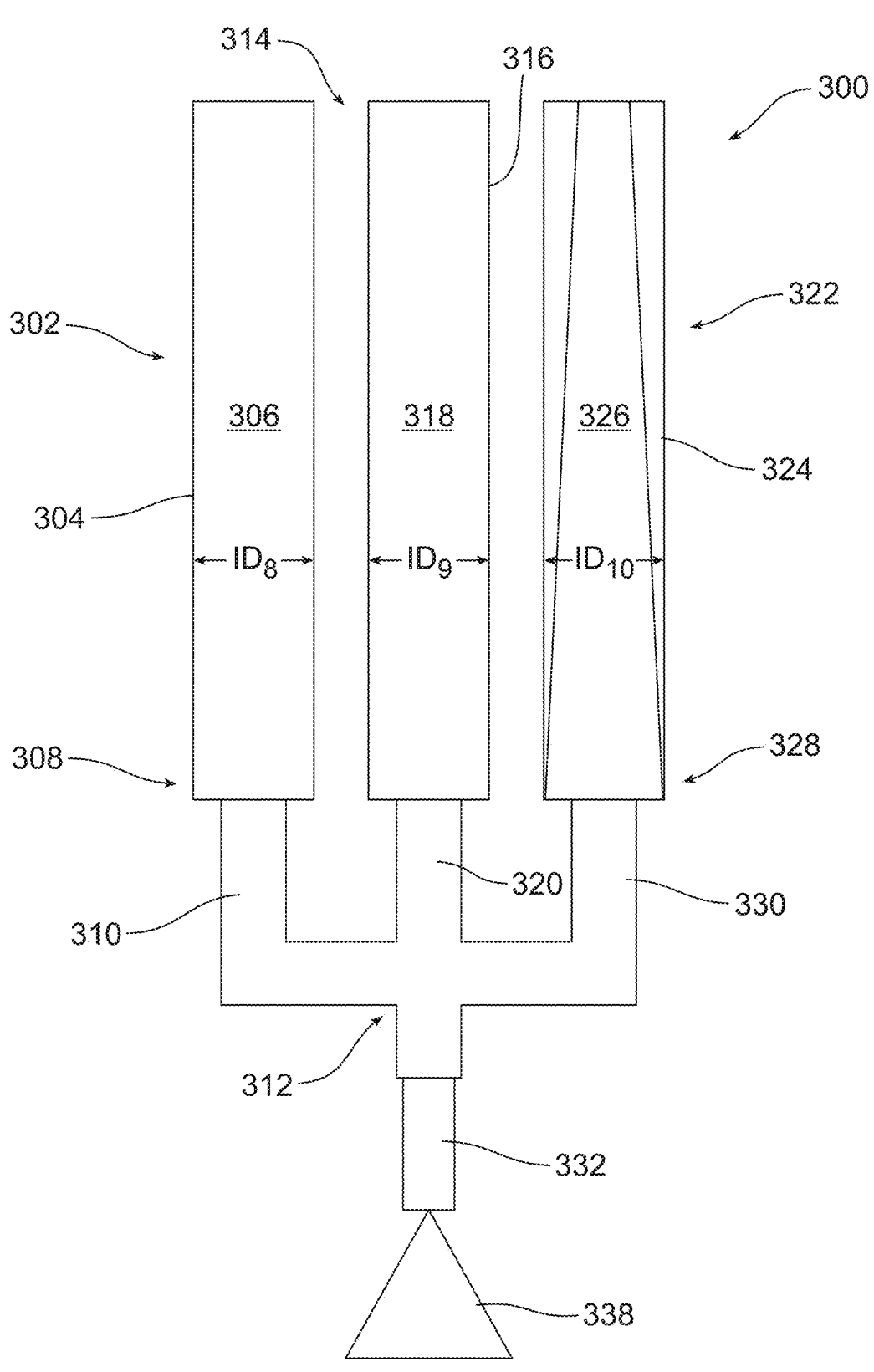
FIG. 8 is a schematic view of an applicator instrument used for mixing a first fluid having a first reactive component, a second fluid having a second reactive component, and a pH modifying fluid, whereby the rate at which the pH modifying fluid is added to the mixture is increased between a first stage and a second stage, in accordance with one embodiment of the present patent application.

Referring to FIG. 8, in one embodiment, an applicator instrument 300 for dispensing a biocompatible sealing composition that is used for sealing tissue and/or hemostasis preferably includes a first syringe 302 having a first barrel 304 that defines a first chamber 306. In one embodiment, the first chamber 306 is adapted to receive a first fluid having a first reactive component (e.g., an electrophile). The first barrel 304 preferably has a distal end 308 that is in fluid communication with a first dispensing conduit 310, which is configured to direct the first fluid into a mixing chamber 312 of the applicator instrument 300. In one embodiment, the inner diameter $ID_8$ of the first barrel 304 preferably remains constant between the proximal end and the distal end 308 thereof. Although not shown, a rod and piston may be used for forcing the first fluid from the distal end 308 of the first barrel 304.

In one embodiment, the applicator instrument 300 preferably includes a second syringe 314 having a second barrel 316 that defines a second chamber 318. In one embodiment, the second chamber 318 is adapted to receive a second fluid having a second reactive component (e.g., a nucleophile). The second barrel 316 preferably has a distal end 318 that is in fluid communication with a second dispensing conduit 320, which is configured to direct the second fluid into the mixing chamber 312 of the applicator instrument 300, whereby the first and second fluids are mixed together and react to form the biocompatible sealing composition. In one embodiment, the inner diameter $ID_9$ of the second barrel 316 desirably remains constant between the proximal end and the distal end thereof. Although not shown, a rod and piston may be used for forcing the second fluid from the distal end of the second barrel 316.

In one embodiment, the inner diameters $ID_8$ and $ID_9$ of the respective first and second barrels 204, 216 are the same. In one embodiment, the first and second fluids may be jointly expressed in a constant ratio (e.g., a constant flow rate). In one embodiment, the first and second fluids may be jointly expressed in a 1:1 ratio.

In one embodiment, the applicator instrument 300 preferably includes a third syringe 322 having a third barrel 324 that defines a third chamber 326. In one embodiment, the third chamber 326 is adapted to receive a pH modifying fluid (e.g., NaOH having a 10-14 pH), which is added into the mixture of the first and second fluids for controlling the rate of cross-linking of the first and second reactive components of the respective first and second fluids. The third barrel 324 preferably has a distal end 328 that is in fluid communication with a third dispensing conduit 330, which is configured to direct the pH modifying fluid into the mixing chamber 312 of the applicator instrument 300. In one embodiment, the inner diameter $ID_{10}$ of the third barrel 324 desirably changes in size between the proximal end and the distal end 328 thereof, which changes and/or varies the flow rate of the pH modifying fluid into the mixing chamber 312 of the applicator instrument 300. In one embodiment, the inner diameter $ID_{10}$ of the third barrel 224 is smaller at the proximal end thereof and larger at the distal end 228 thereof. In one embodiment, the inner diameter $ID_{10}$ of the third barrel 324 gradually increases in size between the proximal end and the distal end 328 thereof.

In one embodiment, the applicator instrument 300 preferably includes a nozzle 332 that is in fluid communication with the mixing chamber 312 and that has one or more dispensing orifices that are adapted to dispense a mixture of the first fluid, the second fluid, and the pH modifying fluid. In one embodiment, the mixture of the first fluid, the second fluid, and the pH modifying fluid may be dispensed as a spray that is directed toward a target on a surface (e.g., a tissue surface; a blood vessel). In one embodiment, the nozzle 332 may be adapted to drip the mixture of the first fluid, the second fluid, and the pH modifying fluid onto a surface. The expressed mixture preferably forms a sealing formulation 338 that is applied onto a target such as tissue of a patient.

In one embodiment, prior to being expressed from the nozzle 332 of the applicator instrument 300, the first fluid having the first reactive component and the second fluid having the second reactive component are mixed together in the mixing chamber 312. The pH modifying fluid in the third chamber 326 is added to the mixture of the first and second fluids in a changing ratio. In one embodiment, a lower rate of pH modifying fluid is added to the mixture at the beginning of an expression and a higher rate of the pH modifying fluid is added to the mixture at the end of the expression. At the lower rate of adding the pH modifying fluid, the cross-linking of the first and second reactive components occurs at a lower and/or slower rate. At the higher rate of adding the pH modifying fluid, the cross-linking of the first and second reactive components occurs at a higher and/or faster rate.

In one embodiment, a lower ratio of the pH modifying fluid is added to the mixture during a first stage of an expressing the mixture step and a higher ratio of the pH modifying fluid is added to the mixture during a second stage of the expressing the mixture step.

In one embodiment, each of the first and second fluids is expressed at a uniform flow rate throughout an expressing the mixture step, and the pH modifying fluid has a lower flow rate during a first stage (e.g., the beginning) of the expressing the mixture step and a higher flow rate during a second stage (e.g., the ending) of the expressing the mixture step.

In one embodiment, the lower flow rate of the pH modifying fluid is 0.5-1.0 mL/minute and the higher flow rate of said pH modifying fluid is 3-6 mL/minute.

In one embodiment, during the first stage (e.g., the beginning) of the expressing the mixture step, a mixing ratio of the pH modifying fluid, the first fluid and the second fluid is 0.12-0.24:1:1. In one embodiment, during the second stage (e.g., the ending) of the expressing the mixture step, the mixing ratio of the pH modifying fluid, the first fluid and the second fluid is 0.7-1.4:1:1. Thus, the pH modifying fluid is added at a lower rate during the first stage and at a higher rate during the second stage of the expressing the mixture step.

In one embodiment, during the first stage of the expressing the mixture step, the first and second reactive components have a lower cross-linking rate. In one embodiment, during the second stage of the expressing the mixture step, the first and second reactive components have a higher cross-linking rate. The different cross-linking rates will affect the physiological structure of the biocompatible sealing composition that is formed on a surface (e.g., a tissue surface).

Figure 9:
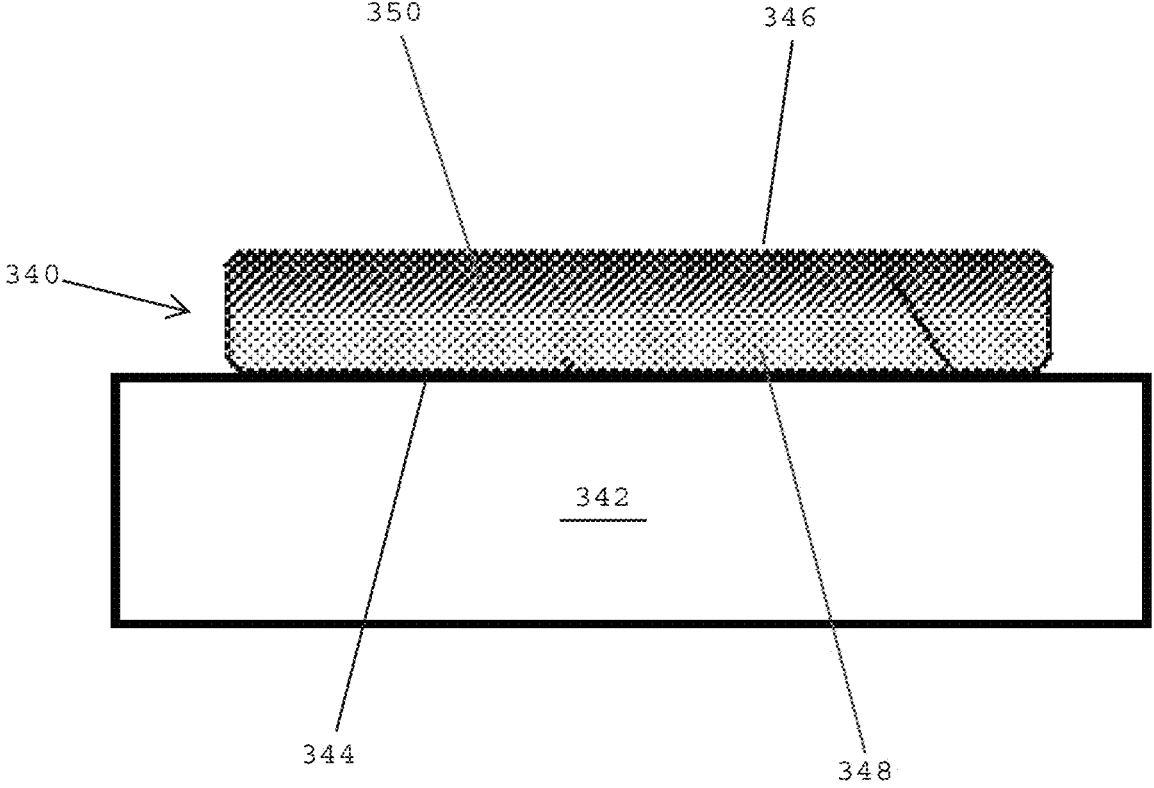
FIG. 9 shows a sealing composition that is formed using the applicator instrument of FIG. 8 and resulting from an increase in the rate at which a pH modifying fluid is added to a mixture of a first fluid having a first reactive component and a second fluid having a second reactive component, in accordance with one embodiment of the present patent application.

FIG. 9 shows a biocompatible sealing composition 340 that has been formed on tissue 342, which has been created using the applicator instrument 300 and the flow rate ratios described above in FIG. 8. The biocompatible sealing composition 340 has a bottom surface 344 that faces toward the tissue 342 and a top surface 346 that faces away from the tissue 342. The biocompatible sealing composition 340 formed on the tissue 342 has a mixing ratio of components gradually changing from a lower cross-linking percentage within a bottom zone 348 of the sealing composition 340 to a higher cross-linking percentage within a top zone 350 of the sealing composition 340. The gradual change in cross-linking is schematically indicated in FIG. 9 by a shading gradient, whereby the darker region indicates a higher rate of cross-linking of the reactive components and the lighter region indicates a lower rate of cross-linking of the reactive components.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of making a biocompatible composition for sealing tissue comprising:
    mixing a first fluid having a first reactive component and a second fluid having a second reactive component to form a mixture;
    expressing the mixture of said first and second fluids;
    during the expressing the mixture step, adding a pH modifying fluid to the mixture, wherein the rate at which said pH modifying fluid is added to the mixture changes during the expressing step for changing cross-linking reaction rates between said first and second reactive components.

2. The method as claimed in claim 1, wherein a higher ratio of said pH modifying fluid is added to the mixture during a first stage of the expressing the mixture step and a lower ratio of said pH modifying fluid is added to the mixture during a second stage of the expressing the mixture step.

3. The method as claimed in claim 2, wherein each of said first and second fluids is expressed at a uniform flow rate throughout the expressing the mixture step, and wherein said pH modifying fluid has a higher flow rate during the first stage of the expressing the mixture step and a lower flow rate during the second stage of the expressing the mixture step.

4. The method as claimed in claim 3, wherein the higher flow rate of said pH modifying fluid is 3-6 mL/minute and the lower flow rate of said pH modifying fluid is 0.5-1.0 mL/minute.

5. The method as claimed in claim 3, wherein during the first stage of the expressing the mixture step, a mixing ratio of said pH modifying fluid, said first fluid and said second fluid is 0.7-1.4:1:1, and wherein during the second stage of the expressing the mixture step, the mixing ratio of said pH modifying fluid, said first fluid and said second fluid is 0.12-0.24:1:1.

6. The method as claimed in claim 2, wherein during the first stage of the expressing the mixture step, said first and second reactive components have a higher cross-linking rate, and wherein during the second stage of the expressing the mixture step, said first and second reactive components have a lower cross-linking rate.

7. The method as claimed in claim 1, wherein the expressing the mixture step further comprises spraying or dripping the mixture onto a surface to form said biocompatible composition on the surface.

8. The method as claimed in claim 1, wherein said first reactive component comprises an electrophilic polymer material and said second reactive component comprises a nucleophilic material.

9. The method as claimed in claim 8, wherein said electrophilic polymer material comprises electrophilic PEG and said nucleophilic material comprises PEG-Amine or albumin.

10. The method as claimed in claim 9, wherein said electrophilic PEG comprises PEG-NHS.

11. The method as claimed in claim 1, wherein said pH modifying fluid has a pH level of between pH 10-pH 14.

12. The method as claimed in claim 1, wherein said pH modifying fluid comprises NaOH.

13. The method as claimed in claim 1, wherein said first fluid comprises 150 mg/mL 4 Arm PEG-SG-20K and 100 mM carbonate buffer having pH 9.0, said second fluid comprises 200 mg/mL albumin in water, and said pH modifying fluid comprises 1N NaOH.

14. The method as claimed in claim 1, wherein each of said first and second fluids is expressed at a uniform flow rate throughout the expressing the mixture step, wherein said pH modifying fluid has a lower flow rate during the first stage of the expressing the mixture step and a higher flow rate during the second stage of the expressing the mixture step.

15. The method as claimed in claim 14, wherein during the first stage of the expressing the mixture step, said first and second reactive components have a lower cross-linking rate, and wherein during the second stage of the expressing the mixture step, said first and second reactive components have a higher cross-linking rate.

16. The method as claimed in claim 14, wherein the lower flow rate of said pH modifying fluid is 0.5-1.0 mL/minute and the higher flow rate of said pH modifying fluid is 3-6 mL/minute.

17. The method as claimed in claim 16, wherein during the first stage of the expressing the mixture step, a mixing ratio of said pH modifying fluid, said first fluid and said second fluid is 0.12-0.24:1:1, and wherein during the second stage of the expressing the mixture step, the mixing ratio of said pH modifying fluid, said first fluid and said second fluid is 0.7-1.4:1:1.

18. A method of making a biocompatible sealing composition comprising:

mixing a first fluid having a first reactive component, a second fluid having a second reactive component, and a pH modifying fluid to form a mixture;

expressing the mixture of said first fluid, said second fluid, and said pH modifying fluid to form said biocompatible sealing composition having different zones with different rates of cross-linking;

during the expressing the mixture step, changing the mixing ratio of said pH modifying fluid relative to said first and second fluids for modifying cross-linking rates of said first and second fluids throughout the different zones of said biocompatible sealing composition.

19. The method as claimed in claim 18, wherein during one stage of the expressing the mixture step, a mixing ratio of said pH modifying fluid, said first fluid and said second fluid is 0.7-1.4:1:1, and wherein during another stage of the expressing the mixture step, the mixing ratio of said pH modifying fluid, said first fluid and said second fluid is 0.12-0.24:1:1.

20. The method as claimed in claim 18, wherein said first reactive component comprises an electrophile, said second reactive component comprises a nucleophile, and said pH modifying fluid comprises NaOH and has a pH level of between pH 10 and pH 14.

* * * * *